United States Patent [19]

Jain et al.

[11] Patent Number: 5,153,166
[45] Date of Patent: Oct. 6, 1992

[54] CHROMATOGRAPHIC STATIONARY SUPPORTS

[75] Inventors: Tikam Jain, King of Prussia; Robert Shorr, Overbrook Hills, both of Pa.

[73] Assignee: Trustees of AT Biochem, Malvern, Pa.

[21] Appl. No.: 233,596

[22] Filed: Aug. 18, 1988

[51] Int. Cl.$^5$ .............................................. B01J 20/26
[52] U.S. Cl. ..................................... 502/402; 502/401; 502/403; 502/404; 530/811; 530/812; 530/813; 530/814; 530/815; 530/816
[58] Field of Search ............... 502/401, 402, 403, 404, 502/7; 530/811, 812, 813, 814, 815, 816

[56] References Cited

U.S. PATENT DOCUMENTS

| | | | |
|---|---|---|---|
| 3,910,825 | 10/1975 | Huper et al. | 530/816 X |
| 3,987,058 | 10/1976 | Saunders et al. | 502/401 X |
| 4,308,254 | 12/1981 | Tayot et al. | 424/124 |
| 4,317,810 | 3/1982 | Halbert et al. | 530/816 X |
| 4,325,658 | 4/1982 | Baker | 405/264 |
| 4,351,846 | 9/1982 | Matsumoto et al. | 424/305 |
| 4,370,476 | 1/1983 | Usher et al. | 536/113 |
| 4,407,795 | 10/1983 | Nicolau et al. | 424/180 |
| 4,419,444 | 12/1983 | Quash | 435/7 |
| 4,430,229 | 2/1984 | Yamawaki et al. | 502/401 X |
| 4,520,122 | 5/1985 | Arena | 502/152 |
| 4,525,465 | 6/1985 | Someno et al. | 502/7 |
| 4,532,232 | 7/1985 | Larsson et al. | 502/403 |
| 4,604,207 | 8/1986 | Oi et al. | 210/635 |
| 4,606,825 | 8/1986 | Crane et al. | 210/635 |
| 4,659,504 | 4/1987 | Hayes | 252/315.3 |
| 4,661,248 | 4/1987 | Ramsden et al. | 210/198.2 |
| 4,663,313 | 5/1987 | Bristol et al. | 514/46 |
| 4,680,120 | 7/1987 | Ramsden et al. | 210/635 |
| 4,680,121 | 7/1987 | Ramsden et al. | 210/635 |
| 4,699,784 | 10/1987 | Shih et al. | 424/85 |
| 4,753,983 | 6/1988 | Ngo | 525/54.1 |

FOREIGN PATENT DOCUMENTS

| | | |
|---|---|---|
| 263934 | 4/1988 | European Pat. Off. . |
| 2263289 | 7/1974 | Fed. Rep. of Germany ...... 530/813 |
| 53-75323 | 7/1978 | Japan ....................................... 502/7 |
| WO83/03776 | 4/1982 | PCT Int'l Appl. . |
| 1223281 | 2/1971 | United Kingdom ................. 530/814 |
| 1441979 | 7/1976 | United Kingdom ................. 530/813 |

OTHER PUBLICATIONS

Hollis, et al., "Fast Affinity Chromatography Using Small Particle Silica-Based Packing Materials," *J. Liq. Chromat.*, 10, 2349 (1987).
Iler, Ralph K., *The Chemistry of Silica*, John Wlley & Sons, New York, pp. 598–599.
Volkova, A. N. et al., *Zh. Obshch. Khim.*, 43, 724 (1973).
Low, M. J. D. et al., *Chem. Commun.*, 1967 (12) 609.
Brust, Otto-Ernst, et al., *Journal of Chromatography*, 83 (1973) 15–24.

*Primary Examiner*—Patrick P. Garvin
*Attorney, Agent, or Firm*—Woodcock Washburn Kurtz MacKiewicz & Norris

[57] ABSTRACT

Methods for modifying polyhydroxylated materials by the direct covalent bonding of nucleophilic ligands to the former sites of hydroxyl groups on the material are disclosed. More specifically, methods for activating the surface of polyhydroxylated materials such as silica, which can serve as stationary phases in various chromatographic methods, are disclosed. The silica is first contacted with a reagent, e.g., a phosphorylating agent, effective to cleave the O—H bond of at least one of said hydroxyl groups and introduce through an —O— linkage a moiety amenable to nucleophilic displacement; and the product of step (a) is then contacted with a suitable nucleophilic ligand.

18 Claims, 7 Drawing Sheets

CHROMATOGRAPHIC STATIONARY SUPPORTS

BACKGROUND OF THE INVENTION

This invention relates to methods for modifying polyhydroxylated materials by covalently bonding nucleophilic ligands to said material. More specifically, this invention relates to improved support materials for use as stationary phases in various chromatographic methods, and to methods for preparing such support materials.

Chromatography is a separation technique whereby individual chemical compounds which were originally present in a mixture are resolved from each other by the selective process of distribution between two heterogeneous (immiscible) phases. The distribution of chemical species to be separated occurs in a dynamic process between a mobile phase and a stationary phase. The stationary phase is a dispersed medium, which usually has a relatively large surface area, through which the mobile phase is allowed to flow. The chemical nature of the stationary phase exercises the primary control over the separation process. The greater the affinity of a particular chemical compound (referred to as the solute) for the stationary medium, the longer it will be retained in the system. The mobile phase can be either gas or liquid; correspondingly, the methods are referred to as gas chromatography and liquid chromatography.

There are a wide variety of chromatographic methods, varying, for example, in the selection of mobile and stationary phases, techniques and solute measurement principles. As an example, ion exchange chromatography is a widely used form of liquid chromatography. It is based on selective ionic attractions between variously charged sample constituents and an ionized chromatographic matrix. The most commonly used ion exchangers consist of an organic polymeric backbone with either acidic or basic exchange sites on its porous surface. The charged resins are capable of exchanging their cations or anions with those ions in the liquid phase which have a greater affinity for the matrix. Exchange interactions that take place during the passage of various ions through the column cause separation into discrete ionic zones.

Thin layer chromatography is a technique in which the stationary phase is a suspension which forms a layer on a plastic or glass plate. It is most frequently an adsorbent (with a particle size of several microns) suspended in a suitable solvent, uniformly spread on a plate, and dried. The mobile phase is a liquid that ascends the plate by capillary action, and the components of the sample mixture are separated by the partition effect.

Reverse-phase chromatography is a type of chromatography in which hydrocarbons as well as polar samples are partitioned between a nonpolar stationary phase and a polar eluting phase. Under these conditions the most polar substances elute most rapidly. This is the reverse of the more common partition chromatography in which the stationary phase is polar and the least polar substances elute most rapidly with the nonpolar eluting phase. In reverse phase chromatography, the stationary phase often consists of a chain of atoms chemically bonded to an inert surface such as silica or glass, and the eluting phase is frequently aqueous methanol or aqueous acetonitrile.

Molecular sieve chromatography, often called gel chromatography, has resulted in tremendous progress in the chemistry of biomacromolecules. Separation in molecular sieve chromatography is based on a selective process of penetration of molecules of different sizes and shapes through a porous gel medium. The largest molecules in the mixture do not penetrate the porous structure at all; the medium-size molecules can penetrate only some pores; and the small molecules can diffuse rather freely inside the medium and can spend a considerably longer time there. Consequently, if the porous material is contained in a column, mixtures of components with differing molecular weights can be effectively resolved.

In any chromatographic process, some components of a given mixture will be retained on the stationary phase longer than others. This allows for extremely selective chromatographic separations. For example, in the method called affinity chromatography, molecules to be purified interact with immobilized ligands on the surface of the stationary phase and are strongly retained by the stationary phase material Passage of a multicomponent extract through a column of immobilized ligand results in selective adsorption of the recognized material to the column. Non-interacting material can be washed away, and bound components can be eluted biospecifically with competetive or affinity modifying reagents, or under denaturing conditions. It is therefore always necessary to seek a stationary phase material with a selectivity appropriate to a given separation problem.

Common to all of the above-described chromatography methods is the use of a stationary phase having at its surface a phase which will interact with the desired components of the mobile phase in the desired manner, e.g., the highly specific ligands attached to the stationary phase in affinity chromatography, or the acidic or basic exchange sites on the stationary phase in ion exchange chromatography. Development of stationary phases for various types of chromatography in general has focused on the attachment of various bonded phases to dextran (Sephadex), agarose, glass, silica and polymeric materials such as polyacrylamide, polymethacrylates or latex.

More specifically, for use in affinity chromatography, the chemistry of ligand immobilization using activation of agarose with cyanogen bromide has been the most popular methodology. The generation of carbonates and caoamates by reaction with 1,1'-carbonyldiimidazole or chloroformate with agarose, polyacrylamide, cellulose, glass beads or hydroxylated polystyrene or other polymers has also been employed. A major disadvantage of such chemistries is the production, on reaction with amines, of a relatively unstable amide bond resulting in continuous ligand leakage at a slow but measureable rate. Moreover, ionic contributions to non-specific protein adsorption are also observed, probably due to the formation of isourea groups. The use of carbonyl diimidizole activated supports which on reaction with amines form a urethane linxage, as well as use of bifunctional oxiranes, has reduced but not eliminated non-specific protein binding. Despite these improvements, agarose remains susceptible to microbial attack, is of limited usefulness in the presence of organic solvents, and is not amenable to easy scale-up and high flow rates. Other supports such as glass, while performing well in organic solvents, suffer from residual charged functions and non-specific binding. Polyacrylamide, while more resistant to microbial attack an agarose, does not form high flow capacity columns. Other polymeric material suffer from higher levels of non-specific interactions than agarose.

Ideally, stationary phases, or chromatography supports, should have good mechanical strength and flow properties, be available in a range of particle sizes, pore sizes and shapes, be chemically stable, possess a high level of hydrophilicity, be amenable to a number of modifications and possess little or no non-specific interaction with the components to be resolved. Silica has been shown to satisfy most of these criteria. Optical activation and performance of silica columns for use in affinity chromatography has been achieved with spherical 10 micron particles. No significant advantage was obtained with smaller particles, and substantial decreases in performance were observed with 20 micron materials. Important advantages accruing from the use of silica supports in affinity chromatography have been found, including high accessible capacity, complete resistance to microbial attack, ease and versatility of immobilization chemistry, high purification efficiency and excellent flow properties. See Hollis et al., *J. Liq. Chromat.*, 10, 2349 (1987). Use of silica results in affinity chromatography systems where elution volumes are minimized and procedures are rapid and easily automated.

Previously, silica has been modified for use in chromatography via a series of reactions using various organosilane analogues and methodologies. These chemistries result in bonded phase attachment via an Si—O—Si linkage which is sensitive and labile to acid, base and other treatments. A generalized scheme representing silane activation of silica is a follows:

Scheme 1

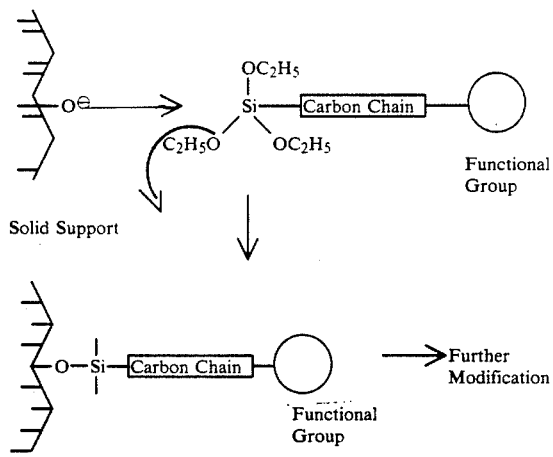

Solid Support

As shown in Scheme 1, the reactive organo silane is directed towards available hydroxyl functions on the silica surface. The half-life of such supports are variable and unpredictable due to slow decomposition of the Si—O—Si bond. In particular, silane activated silicas are unstable above a pH of about 7.2. While this has not hindered the use of silica for applications requiring a pH in the range of 2-7.2, different supports such as polymeric beads must be used for applications requiring a higher pH. Many polymeric beads are stable at elevated pH but show poor flow characteristics and higher non-specific binding when compared to silica. In some cases, zirconium impregnated or polymer coated silicas have been prepared and are claimed to possess higher pH stability.

Thus, although silica provides a chromatographic support material which is advantageous in comparison to other materials in many respects, chemical instability stemming from the chemical approach of attaching a ligand is a severe drawback. There are many separation applications which would benefit from the ability to use a silica support having greater pH stability, e.g., biochromatographic methods involving the separation of proteins, DNA, RNA, cells or cellular particles in a format designed to maintain any associated biological activity. Examples of such biochromatographic techniques are ion exchange, hydrophobic interaction, size exclusion separations, as well as the above-described affinity chromatography. Because of the chemical instability of surface-modified silica, and because optimum bio-separations are usually observed at an alkaline pH, many such biochromatographic separations employ polymer packings possessing less efficient flow properties and substantially greater non-specific interactions than silica.

There is thus a need for methods for preparing silica supports in the absence of impregnated or polymer coating materials which would display little or no non-specific interaction with components to be resolved and which would maintain the excellent flow properties of silica. In addition, there is a need for methods for preparing silica supports which would have greater pH stability than the standard organo silane-activated silicas in use today.

Towards this end, we hypothesized that a silica particle, with its numerous hydroxyl functions, could be viewed as a "polyol" wherein some, if not all, hydroxyls are assumed to be in close proximity and in cis-configuratoin, i.e., as one encounters in a sugar molecule. It is known that a nucleophile may be introduced to a 1,2-cis-diol, such as ribose, by application of carbohydrate phosphate chemistry as illustrated in Scheme 2.

Scheme 2

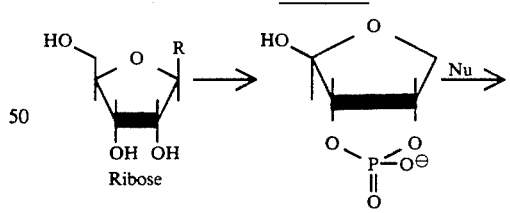

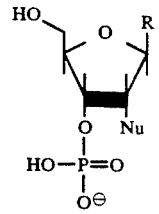

(Nu = nucleophile)

Thus, we hypothesized that a nucleophile could be introduced to a silica surface using the same general chemistry, as illustrated in Scheme 3.

Scheme 3

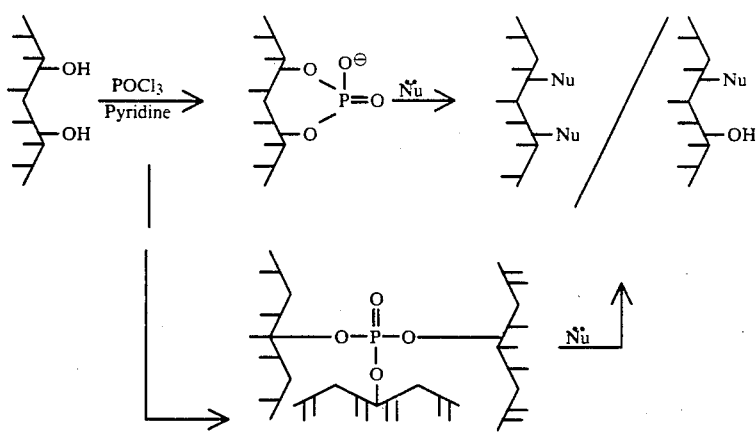

Tests have indicated that such chemistry can indeed be utilized to introduce nucleophiles suitable for chromatography on the surface of silica. Advantageously, in the materials prepared in this manner, the nucleophiles are covalently bound directly to a silicon atom of the backbone, yielding a Si-Nu linkage (Scheme 3) which is more stable than the acid-base-sensitive Si—O—Si—Nu linkage (Scheme 1) arising in standard organo silane-activated silicas, thus avoiding one of the major problems inherent in the use of silica chromatography supports to date. This work has implications far broader, however, than only the modification of silica materials. If it can be assumed that at least a portion of the hydroxyl functions on the surface of a silica support are in close proximity and in cis-configuration, and the work described herein bears out this assumption, then it can also be assumed that at least a portion of the hydroxyl functions on the surface of other polyhydroxylated support materials would also be so arranged. Thus, the activation/nucleophilic displacement chemistry described above can be extended to include the modification of a wide variety of polyhydroxylated materials, exemplified by those described in this patent, in a variety of ways.

SUMMARY OF THE INVENTION

This invention therefore relates to a polyhydroxylated material comprising an organic or inorganic backbone having a plurality of hydroxyl groups at its surface, which material has been modified by the direct covalent bonding to said backbone, at the former site of at least one of said hydroxyl groups, of a nucleophilic ligand. This invention further relates to methods for preparing such materials comprising (a) reacting a polyhydroxylated polymeric material having a plurality of hydroxyl groups at its surface with a reagent effective to cleave the O—H bond of at least one of said hydroxyl groups and introduce through an —O— linkage a moiety amenable to nucleophilic displacement; an (b) reacting the product of step (a) with a nucleophilic ligand.

DETAILED DESCRIPTION OF THE INVENTION

Figure 1:
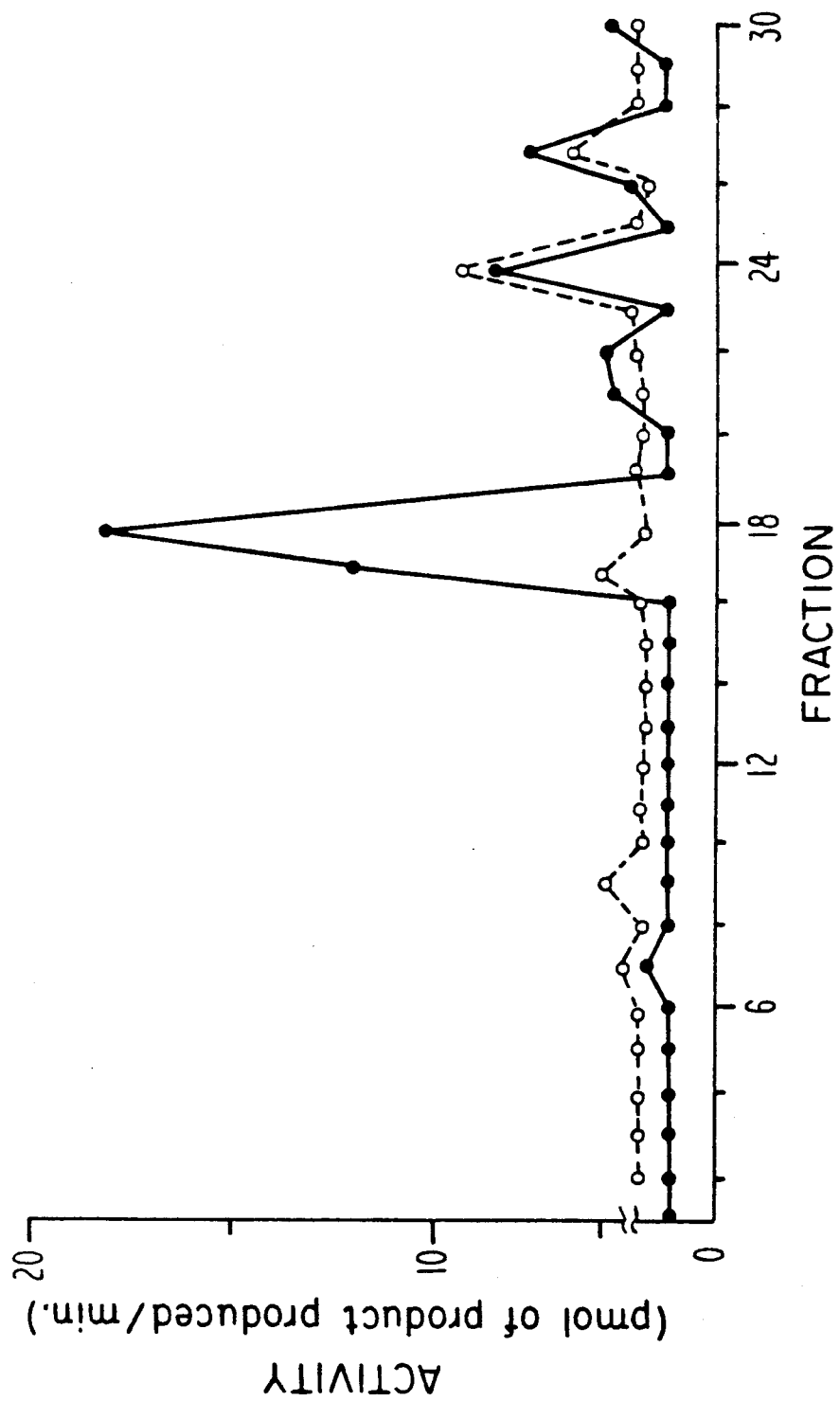
FIG. 1 is a graph of phospholipase A2 and phospholipase c activities of the various fractions collected from a column having a silica support, prepared according to this invention, with mellitin immobilized thereon. The curve with open circles represents endogenous activity and the curve with closed circles represents stimulatory activity.

Tests indicate that the methods described herein can be used to modify, i.e., directly and covalently bond a nucleophile to, the surface of any polyhydroxylated material. By polyhydroxylated, it is meant a material having a plurality of hydroxyl groups on its surface; however the preferred materials for use herein with various surface areas will have far in excess of only two hydroxyl groups. At least a portion of the hydroxyl groups must be at the surface of the support material, e.g., must be accessible to the components of the mobile phase used in the selected chromatographic method. The term "backbone is used herein to refer to the major structure of the polyhydroxylated material to which the hydroxyl groups are bonded. Examples of polyhydroxylated materials which are included within the scope of this invention include those with inorganic backbones such as silica and glass, and those with organic backbones including acrylic resins such as hydroxylated polystyrene/polyvinyl benzene, sepharose, cellulose, agarose, polysaccharides such as dextran and oligosaccharides such as cyclodextrin. Silica, which is the preferred support material, can be used in many forms, including but not limited to particles, beads of any size or shape, blocks, or impregnated into papers of any sort. Similarly, glass may be used in the form of particles, beads, tubes, plates, wool, fibers, capillaries, papers or impregnated glass fiber papers.

The polyhydroxylated material is modified, or activated, by the direct covalent bonding to its surface of a nucleophilic ligand with the specific characteristics required for the intended use of the polyhydroxylated material. By the term "direct" bonding, it is meant that the covalent bond is between the "backbone" of the polyhydroxylated material and an atom of the nucleophile itself, rather than, for example, through the hydroxyl oxygen atom yielding an ether linkage. This invention is not limited by the nature of the ligand, except that it must be nucleophilic in nature (i.e., an electron pair donor). For example, if the polymeric material is intended for use as a stationary phase in affinity chromatography, the ligand may be a material capable of interacting selectively with a component in a mixture to be chromatographed to thereby retain that component on the surface of the stationary phase for later elution. There are myriad other examples of the usefulness of polyhydroxylated polymeric materials modified according to this invention and, thus, of the types of nucleophilic ligands which might be used. These examples include:

Covalent attachment of any chemical, reagent group or material useful for amino acid sequencing by liquid, gas or gas flow techniques, such as polybrene or protein dyes, or functions for protein-peptide immobilization and solid phase sequencing;

Covalent attachment of any chemical, reagent group or material useful for electrophoretic or other transfer; Such groups may contain cleavable acid, base labite, disulfide or other functions. Examples are diethylaminoethylamine, carboxymethylamine, aliphatic or aromatic compounds normally associated with chromatography, polybrene or protein dyes;

Covalent attachment of any material, reagent, protein, DNA, RNA or chemical to a polyhydroxylated material useful for diagnostic or clinical purposes. Examples are attachment to small particles of materials for immunoassay or visualization in vitro or in vivo;

Covalent attachment of any chemical, reagent, natural product, protein, DNA, RNA, for oligonucleotide or peptide and protein synthesis, detection or purification;

Immobilization of enzymes, e.g., proteolytic or synthetic enzymes, for any purpose;

Immobilization of DNA, RNA or nucleotides for any purpose;

Immobilization of antigens, antibodies, antibody binding proteins or any protein or peptide for any purpose;

Immobilization of dyes (fluorescent, colored, radioactive electron dense or other) on sufficiently small particles for any purpose, e.g., for analytical purposes, in vitro or in vivo diagnosis, therapeutics, or detection of any substance separated by any technique or by electron microscopy;

Formation of co- or multi-conjugated particles containing any mixture of materials, chemicals, reagents, dyes or drugs for any purpose such as drug delivery or delivery of signal enhancing markers to specific sites for in vitro or in vivo diagnostics. Further illustrative examples are electron microscopy, fluorescence microscopy, antigen-hapten coupling, delivery to antibody producing cells for immunostimulation or suppression, and covalent attachment to magnetic particles of any substance for any purpose including diagnosis, drug delivery, purification or detection methods;

Immobilization of hydrophobic materials to make them behave in a hydrophilic fashion. Examples include immobilization of radiochromophores for inclusion in electrophoresis gels for replacement of external intensifying screens or for radio-flow detection.

Attachment of materials to mono, di or polysaccharides for any purpose. These include cyclodextrins or polyols of any molecular weight and composition. Materials to be attached, e.g., for drug delivery and diagnostic purposes, include but are not limited to: ligands, drugs, antibodies, antigens, dyes of any sort, specific markers of any sort, antibiotics, and growth factors. Using this approach (or alternate attachment chemistry if experimentally required) cyclodextrins, mono, di or polysaccharides or polyols can be used as bridges between site directed molecules and the functional molecule(s) to be delivered for any purpose. These molecules may be complexed individually or in any combination and proportion for any purpose. The approach is substantially different from the art where liposomes are used to package materials for delivery an in a limited number of cases site-directed molecules used to coat the surface by covalent or non-covalent interactions.

Detection of glycoproteins by contacting said glycoproteins (or a sample containing said glycoproteins) with a reagent (e.g., a phosphorylating agent) effective to cleave the O—H bond of at least one of hydroxyl groups on the glycoproteins and introduce through an —O— linkage a moiety amenable to nucleophilic displacement, followed by reaction with a nucleophilic, fluorescent or radioactive such as fluorescein, dansylamine, rhodamine and their derivatives. In this way, the detectable dye is attached to the glycoprotein, allowing detection of the latter.

The aforementioned applications are exemplary only, and their recitation is not intended to limit the applicability of the chemistry described herein but, rather, to illustrate the broad applicability and versatility of that chemistry.

As further examples of the broad applicability and versatility of the modified polyhydroxylated polymer supports of this invention, the following are examples of targets which might be immobilized on the modified supports in any of the various applications listed above: glycine, gelatin, fucose, N-acetyl glucosamine, D-Ala-D-Ala, adenosine-3',5'-cyclic monophosphate, adenosine-5'-monophosphate, alanine, ε-aminocaproyl glucosamine, benzamidine, ω-aminooctyl, p-aminophenyl-2-acetamido-2-deoxy-β-thioglucopyranoside, m-aminophenyl boronic acid, p-aminophenyl-α galactopyranoside, ω-aminopropyl epoxy, avidin, biton, blue dextran, butyl, chloramphenicol caproate, cholic acid, cholesteryl hemisuccinate, coenzyme-A, concanavalin A (lectins), cysteamine, cytidine 5'-monophosphate, hemoglobin, heparin, S-hexylglutathione, wheat germ lectin, uridine 2', 5'& 3', 5,-diphosphate, uridine 5'-monophosphate, trityl, tryptophan, tyrosine, thyroxine, serine, spermine, oligo dT, protein A, protamine, polyriboinosinic acid, polylysine, O-phosphorylethanolamine, phosphodiesterase 3',5'-cyclid nucleotide activator, octyl, α-methylmannoside, insulin, histidine, lactalbumin, β-nicotinamide adenine dinucleotide, β-nicotinamide adenine dinucleotide phosphate, α-lactose, (+) melibiose, trypsin inhibitor, N-hydroxysuccinimide, imidazolyl carbamate or carbonyl imidiazol moiety, arachidonic acid, polymyxin (endotoxin-removal), 7,7-dimethyleicosadienoic acid, acuvicin (AT-125) (irreversible inhibitor of γ-glutanyl transpeptidase, furegrelate (U-63557A) (thromboxane $A_2$ synthase inhibitor), dopamine antagonists, chiral ligands for resolution of optically active isomers, iminodiacetic acid (metal chelate), polyoxins, p-aminobenzamidine, octadecyl, Cibracon Blue F3Ga, aminoaryl, 8-hydroxyquinoline, Procion Red HE3B, (Nα-CBZ)-D-phenylalanine, poly-(L-lysine), histamine, methotrexate, pepstatin, ketanserin, L-(+)-tartaric acid, serotonin, fetuin, β-estradiol 17-hemisuccinate, glycyl-L-tyrosyl-azo-benzyl succinic acid, deoxycholic acid, diaminodipropylamine, dextran sulfate, p-aminobenzyl phosphonic acid, 2-aminoethyl dihydrogen phosphate, p-aminophenyl phosphoryl choline, boronic acid, p-chloromercuribenzoate, N-acetyl-D,L-homocysteine, L-alanyl-L-alanyl-L-alanine, p-aminobenzamidine, Tris(carboxy methyl)ethylenediamine, 3'-linked deoxyribose with protected pyrimidine or purine base (oligodeoxynucleotide synthesis support), protein G, polybrene, melittin, diethylaminoethylamine, and Coomassie Blue.

Many nucleophilic ligands which could be introduced on the surface of the polyhydroxylated support material according to this invention in order to immobilize targets such as those listed above are generally known in the art. One may use group selective or multispecific ligands for biomolecule purification with affinity chromatography. Examples of group specific ligands are lectins and dyes. Lectins such as concanavalin A or wheat germ agglutinin are proteins which bind to characteristic sugar residues of the carbohydrate portions of glycoproteins. Many lectins from a variety of sources have been identified with differing sugar binding specificities. Glycoproteins bound to immobilized lectins can be eluted with an appropriate free competing sugar. Several dyes have been found to interact selectively with nucleotide requiring enzymes such as dehydrogenase, kinase, peptidase and phosphatase or growth factors. The nature of these interactions is not understood. More selective forms of affinity chromatography use immobilized protein A, protein G, various antigens, antibodies or anti-antibodies. These methods are usually referred to as immunoaffinity chromatography. Immobilized materials such as oligonucletoide binding dyes, etc., can be used for separations of DNA and RNA. Highly specific ligands such as pharmacological ligands and toxins have been used for the affinity chromatography of neurotransmitter and hormone receptors.

For successful affinity chromatography, ligand biomolecule interactions should be on the order of Kd=1-100 nM to allow retention and elution. Appropriate groups for ligand immobilization should be available without compromise of specificity or affinity. Since resin interactions follow mass action kinetics, increasing the concentration of the biomolecule to be purified will drive the reaction forward. The absolute dissociation constant (Kd), however, is characteristic of the biomolecule-ligand system. Adsorbed species are typically in an equilibrium binding state with the immobilized ligand dissociating and reassociating according to ligand-component concentration and system Kd. The concentration of ligand is usually in vast excess over the material to be purified. Immobilization of the ligand may enhance or decrease observed affinities either by steric hinderance or through coupling chemistry.

Biospecific elution can be achieved by using a ligand of higher or similar affinity for the bound component (at a higher or similar concentration) by preventing reinteraction, as the sample dissociates from the resin. Under these conditions purified components are collected in column or batch eluates. In some cases the affinity of a sample for an immobilized ligand can be increased or decreased by an allosteric regulator, modifying agent or changes in mobile phase. Advantage of these properties can be taken in both binding and elution from affinity resins. Eluting ligands are removed by dialysis, gel filtration or another chromatography step. In some cases sample-ligand affinities are such that biospecific elution yields only trace amounts of material. Denaturing agents such as sodium dodecyl sulfate (SDS), urea or changes in ionic strength or pH may be used to recover the sample. Care must be taken that this procedure does not alter the properties of the resin, particularly immobilized lectins or antibodies, protein A or protein G.

The first step involved in the direct covalent bonding of a nucleophilic ligand to the surface of the polyhydroxylated support material involves "activation" of at least a portion of the hydroxyl groups on the surface of the material by cleavage of the 0-H bond and introduction of a moiety amenable to nucleophilic displacement. This is accomplished by contacting the polyhydroxylated material with an agent selected from the group consisting of phosphorylating agents, such as phosphoric acid derivatives or phosphorous oxychloride, sulfonating agents, such as sulfonyl chloride derivatives, and other O-derivatizing agents as set forth below. In this way, the hydroxyl hydrogen is replaced with a moiety amenable to nucleophilic displacement such as a phosphate ester, cyclic phosphate, cyclic anhydride, etc. Examples of reagents which might be used, and the moieties which would thereby be introduced onto the surface of the polyhydroxylated materials through a linkage with the hydroxyl oxygen are as follows:

| Reagent | Moiety |
| --- | --- |
| phosphoryl chloride | $-P(O)_3$ |
| $\begin{array}{c} \text{OH} \\ \vert \\ \text{Hal}-\text{P}-\text{SO}_2\text{OH} \\ \Vert \\ \text{O} \end{array}$ | $-P(O)(OH)SO_2H$ |
| $ClSO_2-Ph-CH_3$ | $-SO_2-Ph-CH_3$ |
| $\begin{array}{c} Cl_3CCNHCOCl \\ \Vert \\ O \end{array}$ | $-OCNHC(O)CCl_3$ |
| $F_3CCH_2SO_2Cl$ | $-SO_2CH_2CF_3$ |

-continued

| Reagent | Moiety |
|---|---|
| O=C(CF₃)(CF₃) | —C(O)CF₃ or —O—C(CF₃)(CF₃)—O— |
| Cl—C(=O)—N(imidazole) | —C(O)—N(imidazole) |
| F-pyridinium/tolyl-SO₃⁻ TsO⁻ | CH₃-pyridinium/tolyl-SO₃⁻ —OTs |

It should be appreciated that structural moieties derived from those specifically recited herein might be found which are amenable to nucleophilic displacement and which could cleave the O—H bonds on the surface of the support material as used herein. Since it is impossible to recite all such moieties, that list presented herein is not intended to be all-encompassing. This invention is deemed to be broad enough to include the use of other structurally related moieties which would function in the same way as the moieties recited herein.

In the preferred embodiment, the polyhydroxylated material is phosphorylated. This may be accomplished by phosphorylation methods generally known in the art. Preferably, the polyhydroxylated material is contacted with an organic base, such as pyridine, and a phosphorylating agent, such as phosphoryl chloride, under anhydrous conditions. The reaction tends to be exothermic. Following removal of the phosphorylating agent, and preferable washing with organic base and alcohol, the phosphorylated material is ready for introduction of the nucleophilic ligand.

Introduction of the nucleophilic ligand is accomplished by contacting the phosphorylated or otherwise "activated" polyhydroxylated support with the nucleophilic ligand under appropriate reaction conditions. Such conditions will vary, according to the selected nucleophile, but, in general, the nucleophilic displacement reaction occurs quite readily and no extraordinary reaction conditions are required.

The materials and methods of this invention, as well as their utility, are further illustrated by the following examples, which are not intended to limit the scope of this invention.

The reactions described in Examples 1 and 3 are illustrated in Scheme 4.

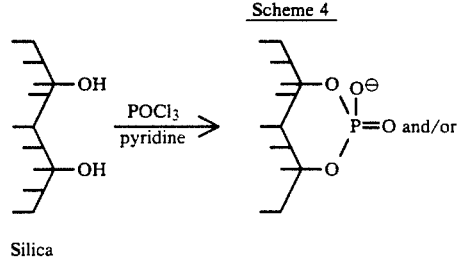

Scheme 4

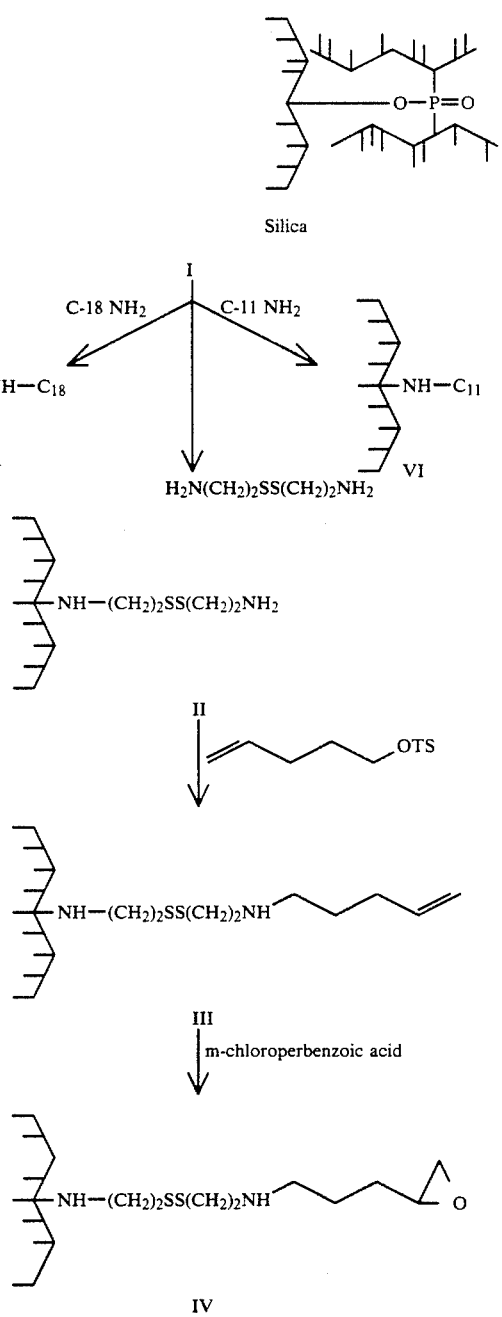

EXAMPLE 1

Preparation of Silica Supports for Chromatography

A. Activation via Phosphorylation

Silica (100 g; 200 micron, 200 Å pore size) was manually stirred at regular intervals with HCl (200 ml, 0.6N) and left standing overnight. After washing with distilled water (10,000 ml) by decantation the silica was collected by filtration in vacuo and over dried at 60° C. for 7 days (Yield: 80 g). 50 g of silica was treated with pyridine (300 ml) and the pyridine distilled off in vacuo until a thick sludge was left behind. After cooling at room temperature, an excess of phosphoryl chloride (50 ml) was added and the solution swirled at regular intervals. The flask was left at 60° C. for 7 days, the silica filtered in vacuo and washed with pyridine. After washing, the silica was vigorously swirled with a large excess of methanol (5000 ml) and allowed to stand overnight in methanol. Modified silica (I) was recovered by filtration. Analysis: Found: P 1.08%; FT-IR(KBr): 1105 cm$^{-1}$ (P=O and P—O stretch).

B. Reaction with Cystamine

Phosphorylated silica (I; 5 g) was mixed with cystamine (7 ml) and left at 60° C. overnight. Ethanol (50 ml) was added to the slurry and refluxed with slow magnetic stirring for 6 hours. Reacted silica was washed with a large excess of ethanol to yield cystaminylated silica (II; 4 g). Analysis: Found; C, 2.32; H, 0.62; N, 1.60%.

C. Tosylation of Cystamine-Silica

Silica (II; 2 g) was stirred overnight at room temperature with acetonitrile containing 4-pentene-1-0-tosylate. Filtration and washing with acetonitrile yielded a light yellow colored product (III). Analysis: Found; C, 2.08; H, 0.51; N, 0.67%.

D. Epoxidation of the Olefinic Moiety of Silica III

Silica III (2 g) containing the 4-pentene moiety was stirred in chloroform (50 ml) containing m-chloroperbenzoic acid (2 g), filtered and washed extensively with chloroform to give the final support (IV) containing the desired epoxy ring. Analysis: Found; C, 4.24; H, 0.75; N, 0.15%.

EXAMPLE 2

Utilization of Silica Supports

A. Purification of Phospholipase Regulatory Protein

Phospholipase enzymes have been shown to play a key role in the proinflammatory production of various eicosanoids and to be subject to a variety of regulatory mechanisms. During the last decade advances have been made in the isolation and characterization of phospholipase and proteins which regulate enzyme activity. A steroid inducible mammalian protein "lipocortin" has been identified, isolated and suggested to exhibit phospholipase $A_2$ ($PLA_2$) activity. Melittin, a bee venom peptide of 2800 MW has been shown to stimulate $PLA_2$ activity. The inventors have used anti-melittin antibodies to isolate from mammalian sources of $PLA_2$ stimulatory protein termed phospholipase activating protein or PLAP. This work used silica affinity columns prepared via silane chemistry or CNBr activated agarose. Substantially better purification folds were obtained with silica than with agarose. The commercially available organo-silane activated silica showed lesser stability under the slightly alkaline pH condition used. The 10 micron particle size reportedly optimal for organo-silane activated silica was also poorly compatible with the biological extracts used. Column fouling therefore occurred after a minimum number of runs. Separation of PLAP using the novel chromatography supports disclosed herein is described below.

Rabbit polyclonal antibodies were prepared against glutaraldehyde crosslinked melittin and affinity purified using melittin immobilized to the silica IV support. The affinity purified antibodies were then immobilized to similar silica and used to isolate cross-reactive material from mammalian cells grown in culture. Stimulatory activity was defined as the difference between the activity observed in reactions containing cell free sonicates and any endogenous activity associated with fractions from the affinity column. One unit of activity was defined as that amount of purified protein required to produce a two-fold increase in observed $PLA_2$ activity found for 1 mg/ml cell free sonicate. Elution and assay of fractions recovered from the antimelittin column revealed material capable of stimulating $PLA_2$ activity. Minimum column fouling occurred and in similar experiments extracts from 16 liters of cultured cells could be chromatographed with no apparent increase in column back pressure or loss of performance. This represents a substantial improvement over the art. A comparison of performance of silica IV at the 20 micron size to organo-silane activated 20 micron silica revealed substantially superior performance for silica IV.

Experimental Details

Approximately 1 mg of synthetic melittin in phosphate buffer (200 mM; pH 7.5) was immobilized to a 4.6 mm×7.5 cm silica IV column (prepared by manual packing of column in acetonitrile) by recirculating at 25° C. overnight at 0.2 ml per minute. Spectral analysis of the recirculate showed 95% immobilization of the applied melittin. After washing with phosphate buffered saline, 2 ml of anti-melittin anti-sera was applied to the column at 0.2 ml/min. After washing, the bound antibody was eluted with 100 mM glycine at pH 3.0. Fractions were collected and the pH was adjusted to 7.5 with phosphate buffer. SDS polyacrylamide gel analysis showed essentially only the heavy and light chains of IgG in the purified preparation.

Affinity Isolation of PLAP

Affinity purified melittin antibodies in PBS were immobilized on a silica IV affinity column by recirculating (0.1 ml/min) 1 ml of affinity purified antibody solution (300 ug/ml) through the column overnight. PBS containing 0.05% Tween 20 was used to wash the column extensively. The column was then equilibrated with PBS containing the protease inhibitors phenylmethylsulfonylfluoride (10 uM), bacitracin, (100 ug/ml), benzamidine (lmM) and soybean trypsin inhibitor (5 ug/ml) and 0.05% Tween 20. Cell sonicate was then passed through the column at 0.1 ml/min. The cell sonicate was prepared as follows. Logarithmically growing cells were removed from five 150 cm$^2$ Corning Tissue Culture Flasks (Corning, NY) and concentrated by centrifugation (500 g for 5 min). Cells were resuspended in 1 ml of Pucks Saline F (GIBCO, Grand Island, NY) containing 10 mM Hepes, protease inhibitors (10 ug/ml soybean trypsin inhibitor; 1 mM benzamidine; 100 ug/ml bacitracin and 10 uM phenylmethylsulfonyl fluoride) and detergents (0.05% Tween 20; 0.04% SDS and 1 mM deoxycholate) and quickly sonicated using a Branson sonicator. Sonicates were centrifuged in a microfuge for 20 min at room temperature and the resulting supernatant passed through a 0.2 um millipore filter (Millipore Corp., Bedford, MA).

The filtered sonicate was passed through the antimelittin antibody column at 0.1 ml/min. The column was washed for 30 min at 2 ml/min followed by elution using 50 mM sodium acetate pH 3.1. Fractions (0.5 ml) were collected and stored frozen at −70° until use.

Phospholipase $A_2$ and phospholipase C activities were quantitated radiometrically using appropriate substrates. Reactions were buffered with 200 mM tris pH 9.0, according to conventional methods. In FIG. 1: the curve with open circle represents endogenous activity. The closed circles represent stimulatory activity.

B. Purification of Phospholipase C

Phospholipase C (PLC) is a term used to refer to a family of enzymes which cleave the polar head group of phospholipids, producing diacylglyceride. Peripheral blood monocytes and polymorphonuclear leukocytes from rheumatoid arthritic patients express elevated PLC activity levels compared to control cells. The elevated activity prefers phosphatidylcholine (PC) as substrate. The microorganism *Bacillus cereus* has been shown to prefer PC as substrate. The inventors have previously used anti-bacterial PLC antibodies and silane activated silica affinity columns to isolate a mammalian PC preferring PLC enzyme. A similar purification using the disclosed silica IV support is described below.

Figure 2:
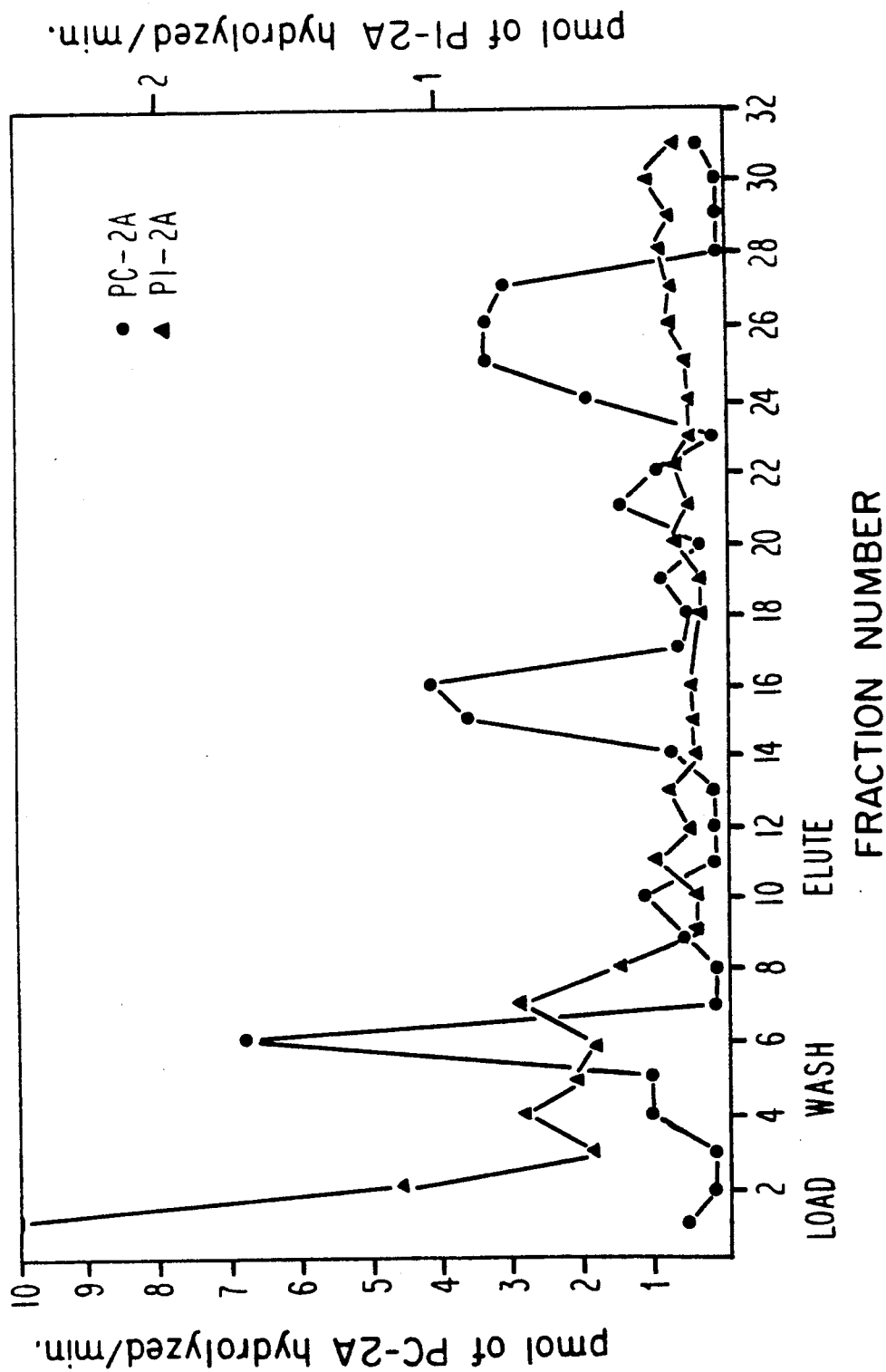
FIG. 2 shows affinity chromatography of phospholipase c on silica prepared according to this invention.

Rabbit polyclonal antibodies were prepared against *Bacillus cereus* PC preferring PLC and affinity purified using the antigen immobilized to silica IV. The affinity purified antibodies were immobilized and used to purify mammalian cross-reactive enzyme from cells grown in culture or drawn from human volunteers. Specifically, affinity purified antibodies, approximately 600 mg, were immobilized on a silica IV column. U937 cells, approximately $10^8$ cells, were sonicated and applied to the column. The column was then eluted and the resulting fractions were assayed for phospholipase C activity using phosphatidylinositol and phosphatidylcholine as substrates. As shown in FIG. 2 this procedure resulted in the recovery of mammalian PC preferring PLC.

Antibody Production and Purification Experimental Details

Phospholipase C isolated from *B. cereus* was obtained from Boehringer Mannheim (Indianapolis, IN) and crosslinked using gluteraldehyde (3% vol:vol) for 30 min at room temperature. The antigen (2000 units per injection) was mixed with a equal volume of Freunds adjuvant and injected intradermally into multiple sites of New Zealand White rabbits at 2 week intervals. The rabbits were bled 3-4 days following the second injections and the blood allowed to clot overnight at 4°. The next day the serum was removed and the immunoglobulin fraction enriched by precipitation using ammonium sulfate. Affinity purified antibodies were then prepared using silica IV as described.

Affinity Chromatography of PLC: Experimental Details

Briefly, 300 ug of affinity purified antibody in 2 ml of phosphate buffered saline (PBS) pH 7.2, (GIBCO, Grand Island, NY) was circulated through a column of silica IV overnight at 0.2 ml/min. The next day the column was washed extensively using PBS containing 0.05% Tween-20 at 2 ml/min. Cells were concentrated by centrifugation (2000×g for 5 min), and resuspended in 2 ml of PBS containing 0.05% Tween-20 and protease inhibitors and sonicated. The protease inhibitors included: phenylmethylsulphonylfluoride (10 uM), bacitracin (100 ug/ml), benzamidine (1 mM) and soybean trypsin inhibitor (5 ug/ml). The cell-free sonicate was then centrifuged in a microfuge (13,000 ×g for 20 min) and the supernatant filtered through a 0.2 uM filter (Millipore, Boston, MA). The filtrate was passed through the anti-PLC antibody affinity column (0.1 ml/min). The mobile phase consisted of PBS with 0.05% Tween-20. The column was then washed using the same mobile phase at 2 ml/min for 10 min and the bound material eluted using 50 mM sodium acetate pH 3.1 at a flow rate of 0.5 ml/min. Fractions were collected (2 ml) in tubes containing 200 ul of 10 x PBS and 400 ul of glycerol.

EXAMPLE 3

Preparation of Silica for Reversed Phase Chromatography

Reversed phase high performance liquid chromatography (HPLC) is a well accepted technique for the separation of many substances. Using the chemistry described herein we have prepared several typical bonded phases on 20 micron 200 A pore sized silica. While these particle and pore sizes are not optimal for reversed phase HPLC separations the materials were used to validate the chemical method.

A. Silica with C-18 and C-11 Moieties

Silica I (5 g) containing a trace amount of pyridine was treated with absolute ethanol (20 ml). The mixture was mechanically stirred and octadecyl amine (5 g) added and the reaction left at 60° C. for 6 days. Finally the solution was refluxed for 6 hours and filtered. The solid was washed with methanol, ethanol, and dried to yield the desired silica with C-18 unit (V; Scheme 4). Analysis: Found; C, 1.59; H, 0.55; N, 0.02%. To prepare silica with C-11 unit undecylamine was used in place of octadecyl amine to yield the desired silica C-11 product (VI; Scheme 4). Analysis: Found; C, 2.85; H, 0.54; N, 0.02%.

Figure 3:
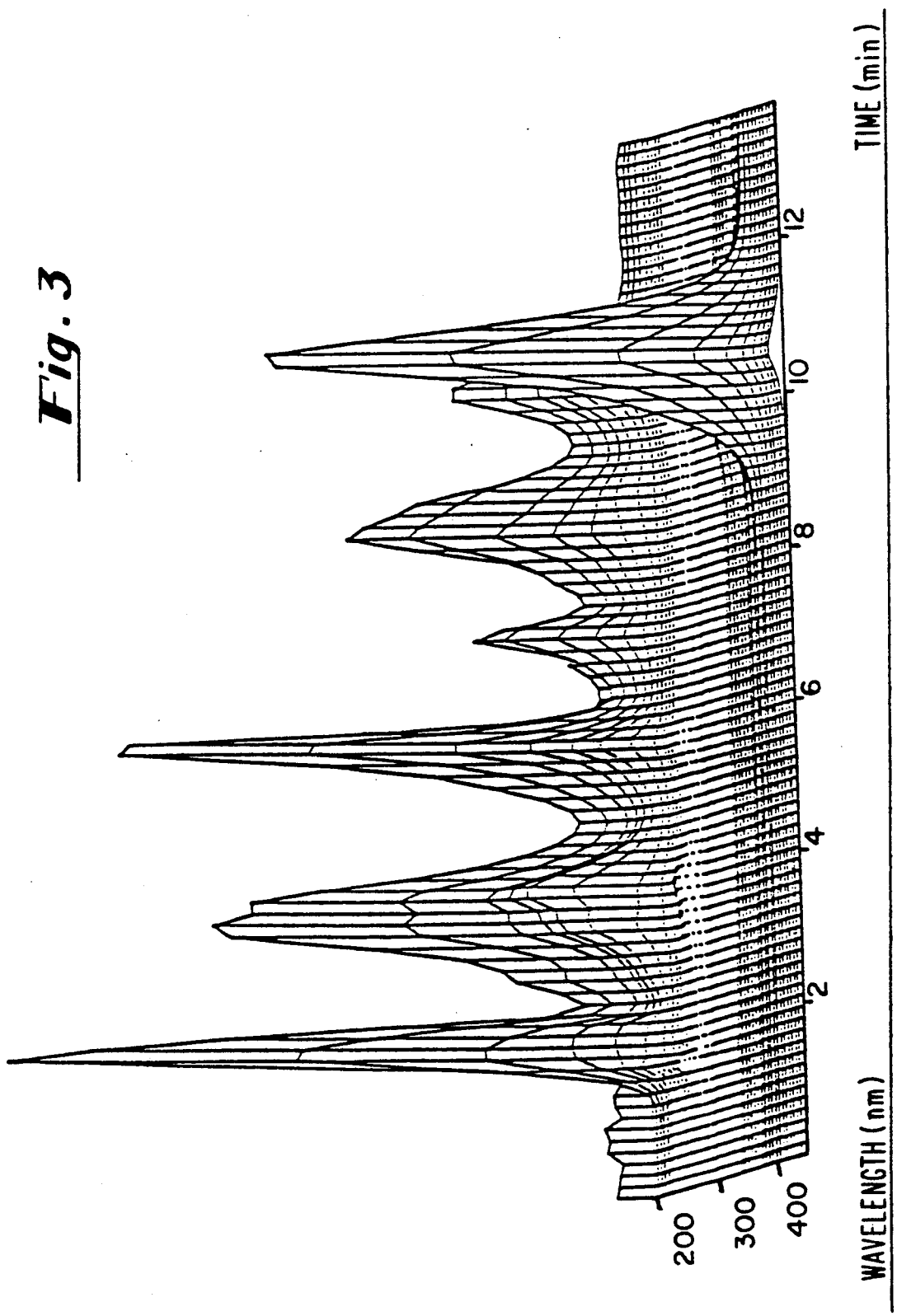
FIG. 3 is the elution profile of cytochrome C tryptic peptides, insulin, cytochrome C, and Bacillus cereus from a column of silica prepared according to this invention, using reversed phase HPLC.
Figure 4:
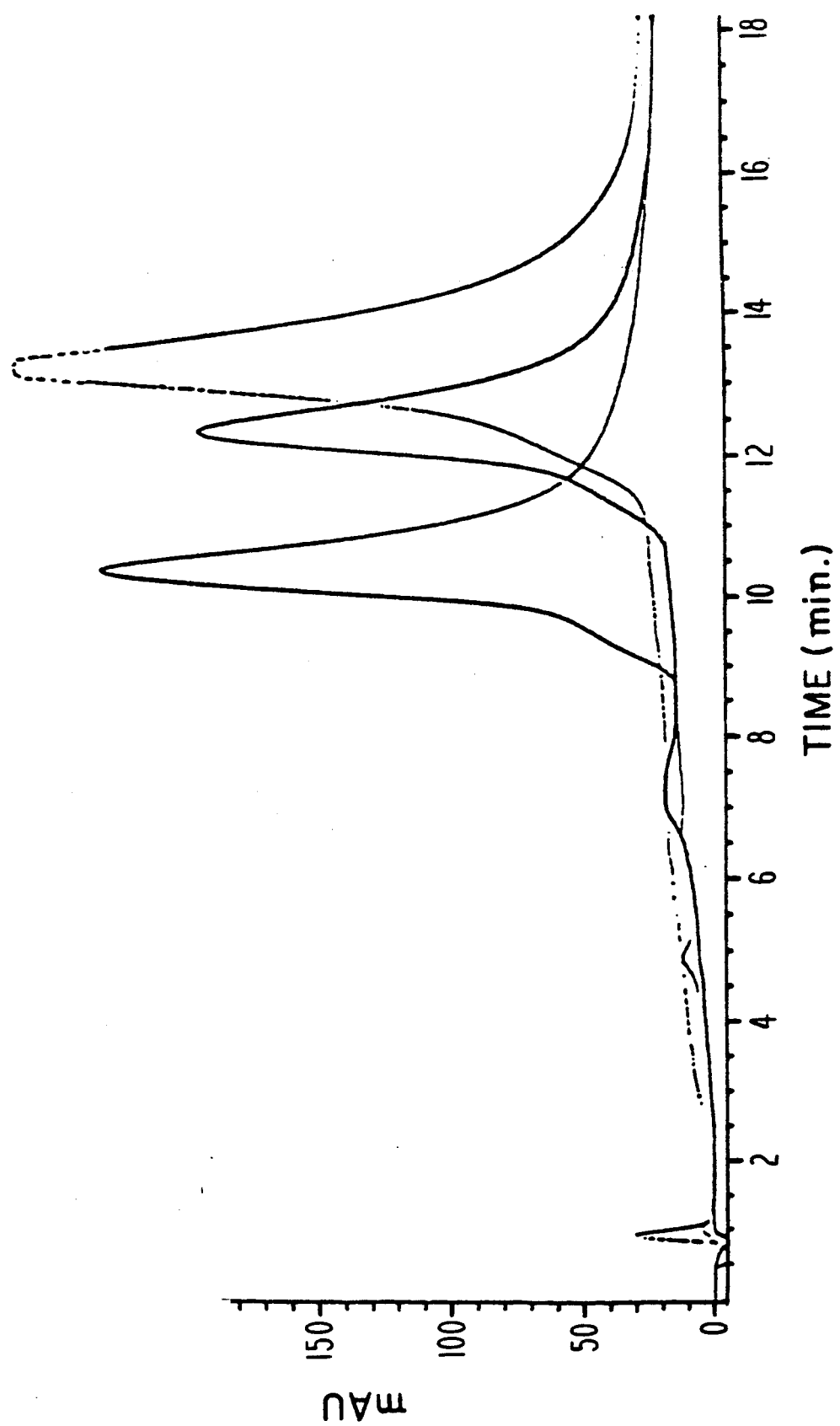
FIG. 4 is the elution profile of cytochrome c, trypsin inhibitor and phospholipase c from a column of silica prepared according to this invention, using reversed phase HPLC and after washing the column with ammonium hydroxide pH 9.5 for 16 hours.
Figure 5:
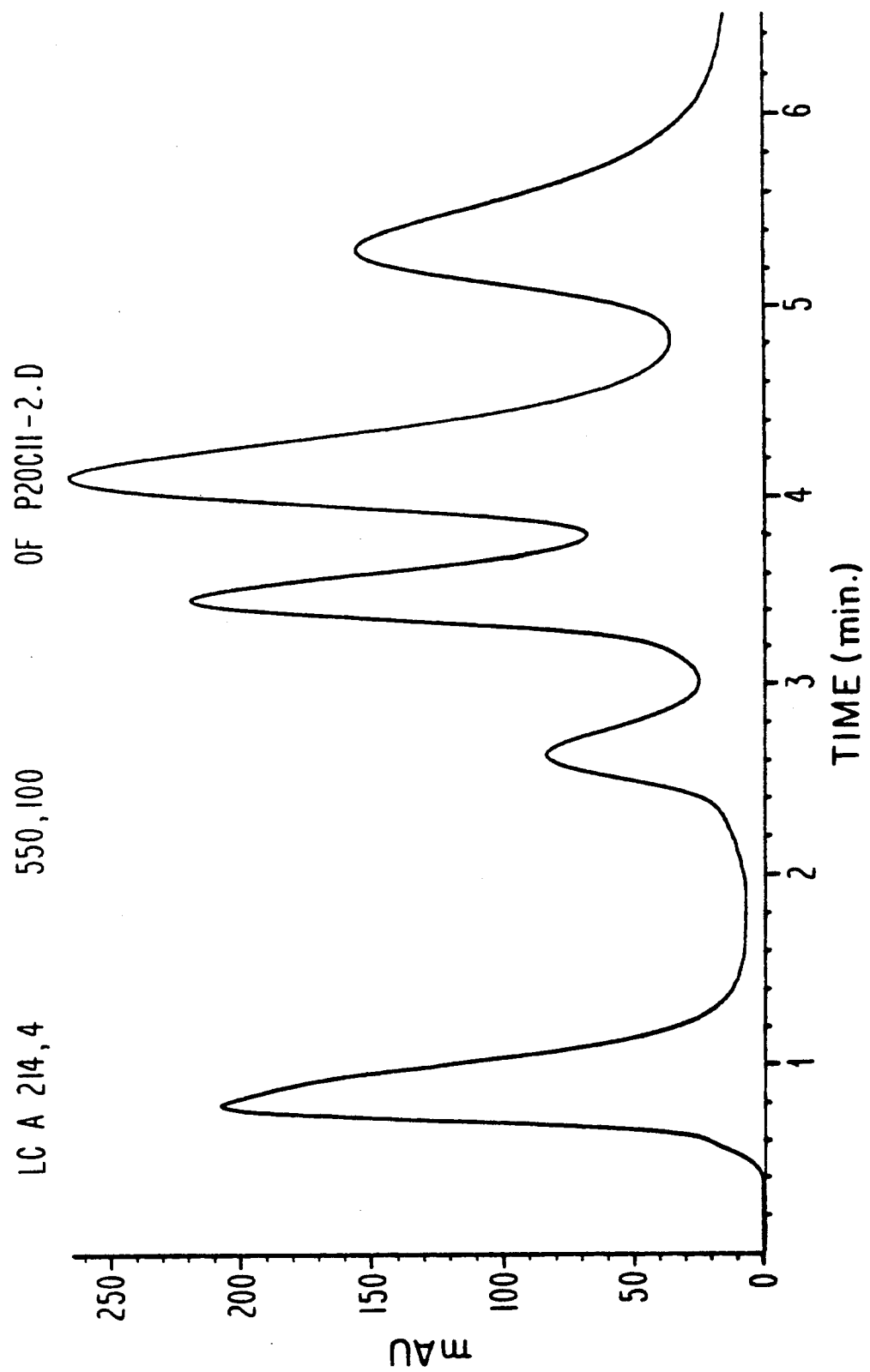
FIG. 5 is the elution profile of small cytochrome c peptides, cytochrome scheme peptide, insulin, cytochrome c and PLC from a column of silica, prepared according to this invention, using reversed phase HPLC.
Figure 6:
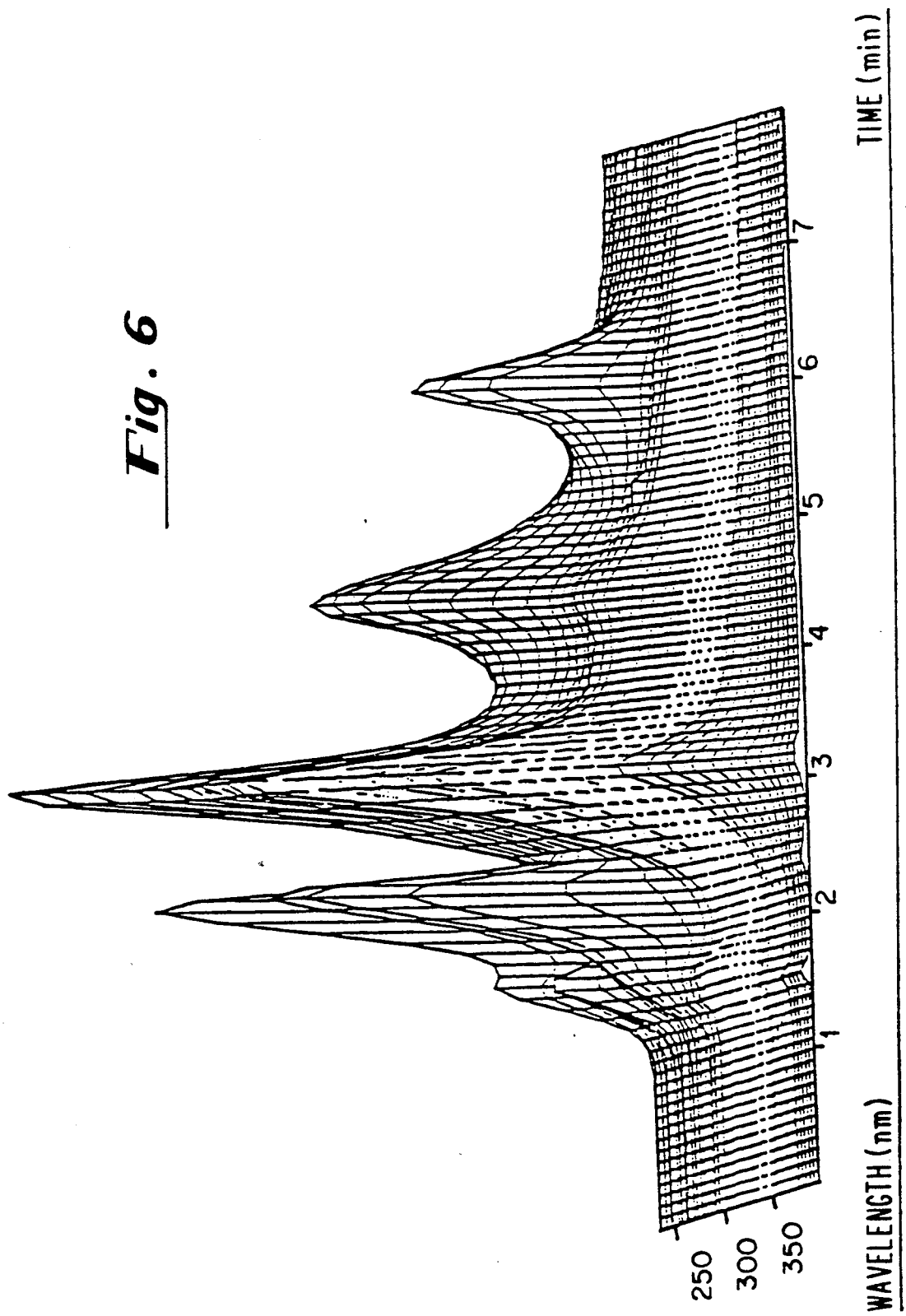
FIG. 6 is the elution profile of a mixture of aromatic amines from a column of silica, prepared according to this invention, using reversed phase HPLC.

B. Separation of Peptides and Proteins by Reversed Phase HPLC Using Silica V and VI Silica V and VI was capped according to the art and 4.6 mm×7.5 cm columns packed by hand in 100% acetonitrile. Mobile phases were 0.1% trifluoroacetic acid (TFA) and 80% acetonitrile. Solvent gradients were produced according to the art using commercially available HPLC systems. Samples were cytochrome C, serum albumin, cytochrome C tryptic peptides, insulin and *Bacillus cereus* PLC. Peaks were detected by diode array ultraviolet absorbance or fixed wavelength detection at 214 nm. Shown in FIG. 3 are the results obtained using a 4.6 mm×7.5 cm column of silica VI. The applied components were cytochrome C tryptic peptides, insulin, cytochrome C, and *Bacillus cereus* PLC. Buffer A was 0.1% TFA. Buffer B was 80% acetonitrile. A linear gradient of 20 to 100% B over 5 minutes was used at a flow rate of 1.5 ml per minute. A similar sample was chromatographed after washing the column with 800 ml of ammonium hydroxide pH 9.5 for 16 hours (FIG. 4). A similar mixture was also chromatographed using silica V (FIG. 5). A separation of aromatic amines on silica V is shown in FIG. 6.

EXAMPLE 4

Preparation of Non-Silica Supports

The reactions described in this example are illustrated in Scheme 5.

Scheme 5
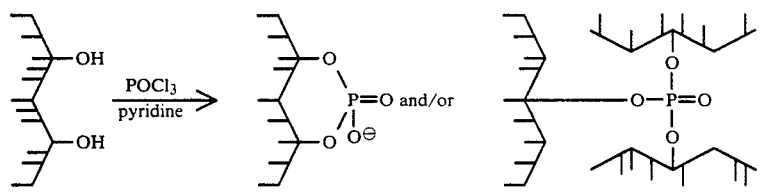
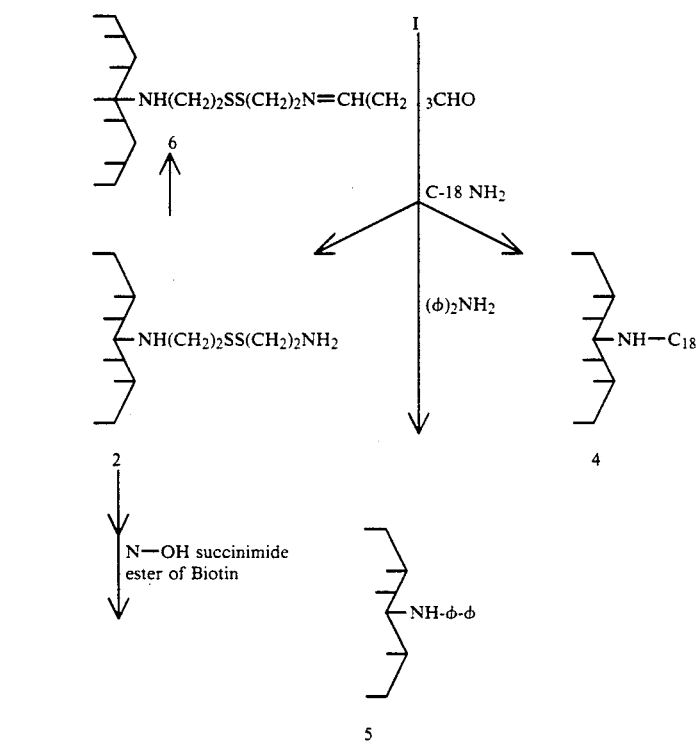
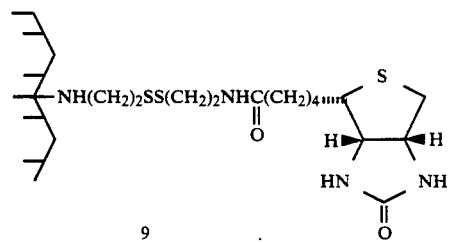
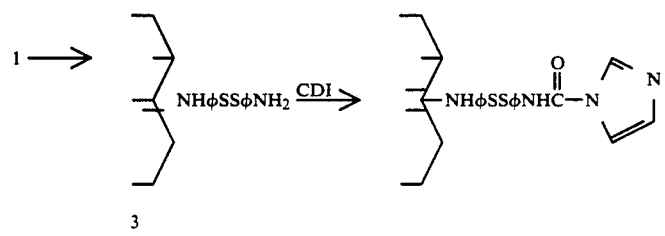

Scheme 5

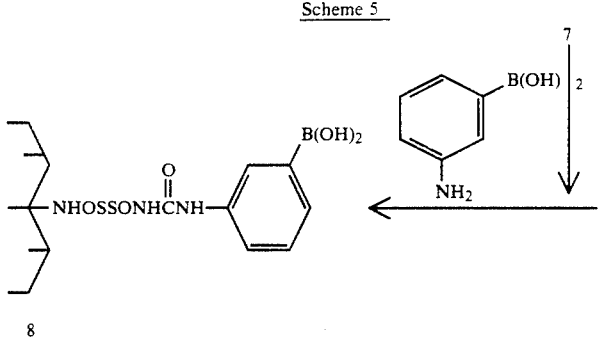

A. Activation via Phoschorylation

Fractogel (hydroxylated polystyrene/polyvinyl benzene, from Toyopearl, TSK HW-65; 32–63 micron; 500 ml) was filtered and the resulting cake swirled with dilute HCl and left standing overnight. After washing with distilled water (5000 ml) and methanol (2000 ml) by decantation the gel was collected by filtration and oven dried at 60° C. for 6 days. 50 g of gel was then slurried with pyridine (300 ml) and the pyridine removed in vacuo until a sludge was left behind. The flask was cooled in a dry ice bath and phosphoryl chloride (50 ml) added slowly to avoid any violent reaction. The flask was left at 60° C. for 2 days. Washing with pyridine, methanol, methanol-water, and methanol yielded the activated Fractogel (1; 40 g). Analysis: Found; H, 6.05; N, 1.14; P, 2.0%.

B. Reaction with Cystamine

Activated Fractogel (1; 5 g) was mixed with cystamine (5 ml) and the resultant slurry left at 60° C. overnight. Absolute ethanol (50 ml) was added and the mixture refluxed overnight. The yellow colored product (2) was recovered by filtration after washing with methanol. Analysis: Found; C, 42.09; H, 5.78; N, 3.09%.

C. Reaction with Diaminodichenyldisulfide

Activated Fractogel (1; 5 g) was reacted with diaminodiphenyldisulfide (5 g) as described for cystamine. The final product 3 showed on analysis: C, 51.42; H, 6.28; N, 2.47%.

D. Reaction with Octadecylamine

Fractogel phosphate (1; 5 g) containing a trace amount of pyridine was slurried with octadecylamine (6 g) and left at 60° C. for 2 days. Toluene (100 ml) was added to the flask and the mixture refluxed for 24 hours. The mixture was then filtered and the gel washed with methanol to yield Fractogel C-18 (4). The resin was capped with methyltrimethoxy silane in toluene-pyridine at 60° C. for 24 hours. Analysis showed; C, 48.82; H, 6.26; N, 5 1.34%.

E. Reaction with Diphenylamine

Fractogel phosphate (1; 5 g) and diphenylamine (5 g) were treated with toluene-pyridine (100:1) and refluxed for 24 hours. Subsequent steps were as described above. The final product Fractogel-diphenylamine (5) showed on analysis: C, 49.36; H, 6.30; N, 2.02%.

F. Reaction with Trimethoxvmethvlsilane

Fractogel with the cystamine chain obtained above (2 g) was stirred in toluene (50 ml) with a trace amount of pyridine. Trimethoxymethylsilane (0.1 ml) was added to the stirring solution and left for 24 hours. Filtration and washing as described above yielded capped Fractogel-cystamine. Analysis showed; C, 47.79; H, 6.60; N, 3.06%.

G. Reaction of Fractocel (2) FII with Glutaraldehyde

Cystamine-containing Fractogel (1; 1 g) was slowly stirred with 1 ml of 50% glutaraldehyde diluted to 4 ml with phosphate buffer pH 7. After 30 minutes at room temperature the reaction mixture at 40° C. was left for 4 days. After washing with methanol, filtration yielded the product (6). Analysis showed; C, 51.18; H; 6.65; N, 2.95%.

H. Preparation of Fractocel-Boronate (8)

Fractogel derivativ (3, 1 g) in acetone (100 ml) was treated with carbonyldiimidazole at 60° C. for 6 days. The product (7) was obtained by filtration and washing with acetone. The imidazole containing product was treated with an equal weight of m-aminophenylboronic acid in 1 M sodium carbonate (20 ml, pH 10) for 4 days at 60° C. The solution was filtered and the final product (8) containing boronic acid (800 mg) obtained. Analysis showed: C, 53.04; H, 6.37; N, 2.80%. FT-IR(KBr): 3600–3100 cm$^{-1}$ (—OH), and 1734 cm$^{-1}$ ( C=0).

I. Preparation of Fractocel-Biotin

Fractogel with cystamine chain (2; 1 g) was treated with the N-hydroxysuccinimide ester of biotin (150 mg) in dimethylformamide (DMF; 4 ml). The reaction mixture was stirred at room temperature for 6 days. The solution was filtered and washed with DMF and pyridine. The biotinylated resin (9) was capped with trimethoxymethylsilane as described above. Analysis showed; C, 48.93; H, 6.46; N, 3.14%.

EXAMPLE 5

Utilization of Fractogel Support

Peptide synthesis is a technique where amino acids are sequentially linked to form peptide chains of various lengths. While the chemistry involved can be performed in solution, several systems have been developed for solid phase peptide synthesis. This technique uses a solid support (usually functionalized polystyrene) and frequently specialized equipment for automated delivery of reagents and solvents. The peptide chain grows on the resin and is cleaved from it after synthesis with hydroflouric (HF) or triflouroacetic acid (TFA). The preferred acid will depend on the nature of the amino acids used. BOC-amino acids require HF, FMOC-amino acids TFA. In addition to the synthesis of peptides for evaluation as therapeutic agents there is an increasing demand for peptides in studies of epitope mapping, purification of proteins, and use specific antibodies for cellular and physiological localization of biomolecules. Assays, diagnostics and a host of other applications also require peptides. These studies are frequently carried out in laboratories with little or no synthetic capabilities. We have sought to prepare reagents that would simplify peptide preparation. A particular advantage would be the elimination of the need for strong acids in cleavage from the resin and recovery of the peptide in a form compatible with HPLC purification as well as ready for attachment to a hapten for antibody production.

Herein we disclose the application of derivatized Fractogel in peptide synthesis. Our starting material was Fractogel containing cystamine which provided two features:

The $NH_2$ group to attach any spacer by nucleophilic displacement.

An S-S bond cleavable under mild conditions.

For synthesis of peptides, an amino acid sequences were chosen to be synthesized and an automated peptide synthesizer used to deliver reagents and solvents.

Figure 7:
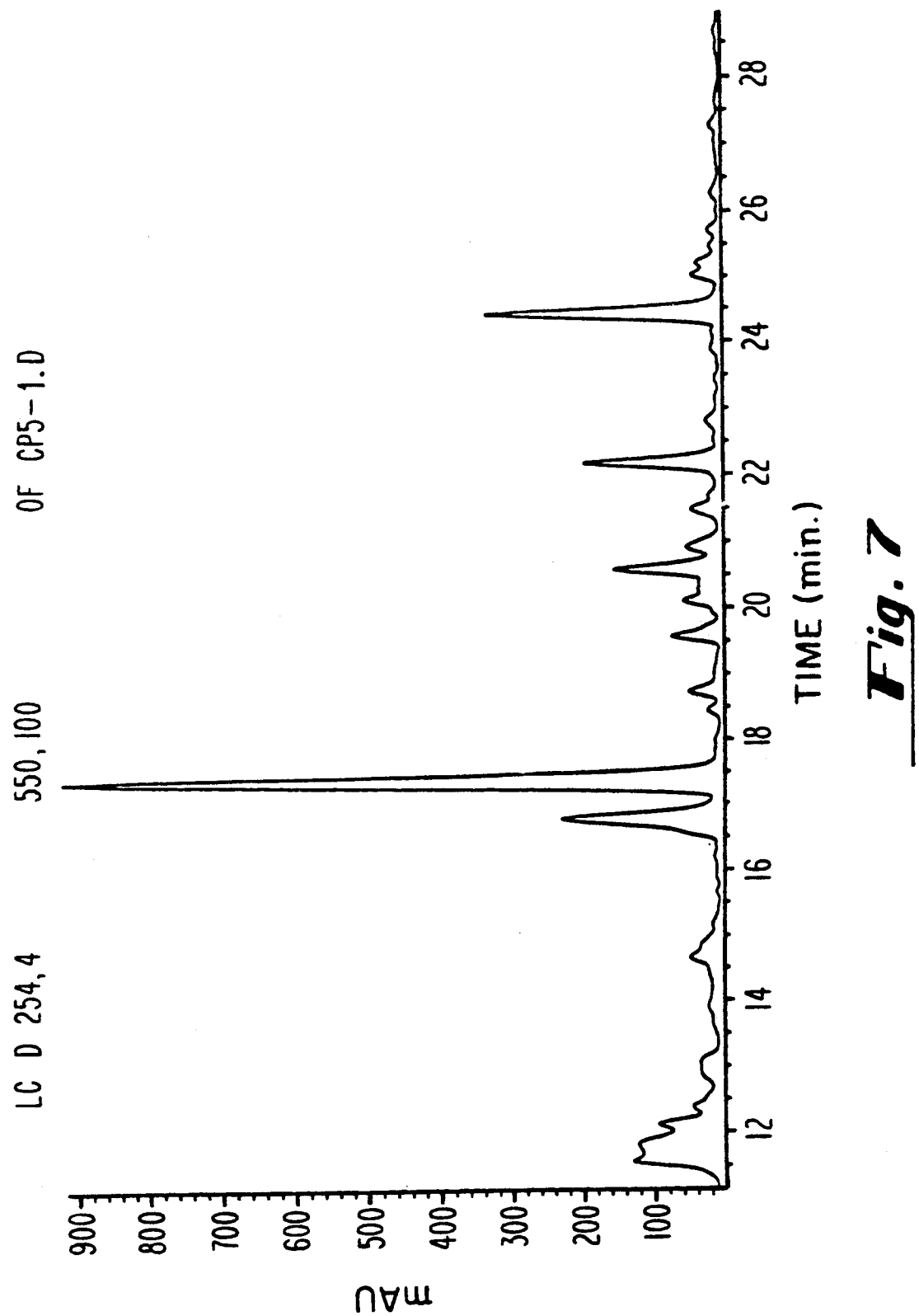
FIG. 7 is the elution profile of the synthetic peptide Gly-Asn-Glu-Phe-Trp-Thr-Ser-Ile-Asp-Val from column using reversed phase HPLC. This peptide was synthesized from components attached to a fractogel prepared according to this invention.

After synthesis the resin was washed with methanol and the peptide cleaved from the resin by reduction of the S—S bond using dithiothreitol or mercaptoethanol. Alternatively the S—S bond was oxidized with performic acid. Organic modifiers such as acetonitrile or detergents necessary for peptide solubility were also added depending on the peptide sequence. (HF or TFA eluted peptides are not frequently recovered in a form compatible with HPLC purification and peptides may be insoluble after removal of the acid). Recovered peptides were directly subjected to HPLC purification and hapten conjugation for antibody production. Amino acid compositions of purified peptides wa confirmed by amino acid analysis. In FIG. 7 are shown the results obtained on synthesis of the peptide Gly-Asn-Phe-Trp-Cys-Glu-Phe-Trp-Thr-Ser-Ile-Asp-Val. This sequence was derived from the deduced sequence for the second extracellular loop of the hamster lung beta adrenergic receptor. The peptide was cleaved from the resin with 1 M dithiothreitol and purified by reversed phase HPLC according to the art. Composition of the recovered peptide was confirmed by amino acid analysis. The recovered peptide contained a free SH group at the site of cleavage and was coupled to the hapten Keyhole Limpet protein for antibody production using SH directed bifunctional crosslinking reagents according to the art.

An alternate approach to the preparation of peptides using readily cleavable S-S functions is to use cis-hydroxyl groups and periodic acid or otherwise acid or base labile bonds. For solution chemistry or as a coupler to already existing resins a BOC or FMOC reagent containing a cleavable function is appropriate. For example BOC or FMOC cystamine. This reagent would preempt the first amino acid in current protocols. All of the above described approaches differ from the art where cleavage occurs at the site of direct attachment to the resin.

Further Improvements to Peptide Synthesis

We suggest that peptide synthesis may also be improved by the use of BOC or FMOC-dipeptides prepared according to the frequency by which such pairs occur in proteins. A similar concept is being explored for oligonucleotide synthesis. By reducing the number of coupling steps for a given synthesis, yield, purity, and achievable chain length should be increased.

What is claimed is:

1. A method for preparing a modified polyhydroxylated material comprising:
   (a) providing a polyhydroxylated material comprising an organic or inorganic backbone having a plurality of hydroxyl groups at its surface;
   (b) contacting said polyhydroxylated material with an agent selected from the group consisting of phosphorylating agents, and compounds of the formulae $Cl_3CC(O) NHCOCl$, $O(CF_3)_2$, and

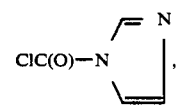

and
   (c) contacting the product of step (b) with a nucleophilic ligand.

2. The method of claim 1 in which said polyhydroxylated material comprises an inorganic backbone.

3. The method of claim 2 in which said polyhydroxylated material is selected from the group consisting of silica and glass.

4. The method of claim 3 in which said polyhydroxylated material is silica.

5. The method of claim 1 in which said polyhydroxylated material comprises an organic backbone.

6. The method of claim 5 in which said polyhydroxylated material is selected from the group consisting of acrylic resins, cellulose, agarose, sepharose, polysaccharides, and oligosaccharides.

7. The method of claim 6 in which said polyhydroxylated material is selected from the group consisting of hydroxylated polystyrene/polyvinyl benzene, dextran, and cyclodextrin.

8. The method of claim 1 in which said nucleophilic ligand is selected from the group consisting of dyes, antibodies, antigens, drugs, antibiotics, lectins, proteins, peptides, amino acids, DNA and RNA.

9. The method of claim 1 in which said agent is a phosphorylating agent.

10. The method of claim 9 in which said agent is selected from the group consisting of phosphorous oxychloride and Hal-P(O)(OH)—$SO_2OH$ were hal=a halogen atom.

11. A method for preparing a modified polyhydroxylated material comprising
    (a) providing a polyhydroxylated material comprising an organic or inorganic backbone having a pluraliyto of hydroxyl groups at its surface;
    (b) contacting said polyhydroxylated material with an agent selected from the group consisting of $ClSO_2$—Ph—$CH_3$ and $F_3CCH_2SO_2Cl$; and
    (c) contacting the product of step (b) with a nucleophilic ligand.

12. The method of claim 1 in which said agent is selected from the group consisting of compounds of the formulae $Cl_3CC(O)NHCOCl$, $O(CF_3)_2$, and

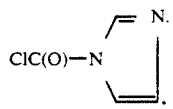

13. The method of claim 3 where said agent is a phosphorylating agent.

14. The method of claim 4 where said agent is a phosphorylating agent.

15. The method of claim 13 where said agent is selected from the group consisting of phosphorous oxychloride and Hal-P(O)(OH)—SO$_2$OH where Hal=a halogen atom.

16. The method of claim 14 where said agent is selected from the group consisting of phosphorous oxychloride and Hal-P(O)(OH)—SO$_2$OH where Hal=a halogen atom.

17. The method of claim 2 where said agent is a phosphorylating agent.

18. The method of claim 17 in which said agent is selected form the group consisting of phosphorous oxychloride and Hal-P(O)(OH)—SO$_2$OH were Hal is a halogen atom.

* * * * *

UNITED STATES PATENT AND TRADEMARK OFFICE
CERTIFICATE OF CORRECTION

PATENT NO. : 5,153,166
DATED : October 6, 1992
INVENTOR(S) : Jain et al.

It is certified that error appears in the above-identified patent and that said Letters Patent is hereby corrected as shown below:

Title page, Column 2, Line 14 delete "WIley" and insert therefor --Wiley--.

Title page, Column 2, Line 22 delete "MacKiewicz" and insert therefor --Mackiewicz--.

Column 2, Line 19 delete "material Passage of" and insert therefor --material. Passage of--.

Column 2, Line 24 delete "competetive" and insert therefor --competitive--.

Column 2, Line 47 delete "caoamates" and insert therefor --carbamates--.

Column 2, Line 59 delete "linxage" and insert therefor --linkage--.

Column 3, Line 1 delete "material" and insert therefor --materials--.

Column 3 line 11 delete "Optical" and insert therefor --Optimal--.

Column 4, Lines 39-40 delete "cis-configuratoin," and insert therefor --cis-configuration,--.

Column 5, Line 59 delete "an" and insert therefor --and--.

UNITED STATES PATENT AND TRADEMARK OFFICE
CERTIFICATE OF CORRECTION

PATENT NO. :     5,153,166

DATED      :     October 6, 1992

INVENTOR(S) :    Jain et al.

It is certified that error appears in the above-identified patent and that said Letters Patent is hereby corrected as shown below:

Column 4, Lines 46 to 54 delete

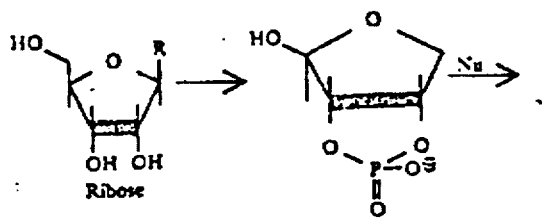

and insert therefor

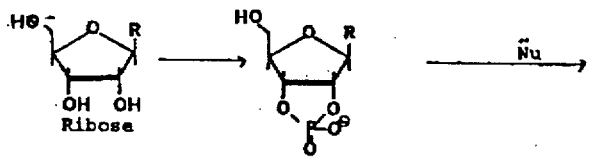

Column

UNITED STATES PATENT AND TRADEMARK OFFICE
CERTIFICATE OF CORRECTION

PATENT NO. : 5,153,166

DATED : October 6, 1992

INVENTOR(S) : Jain et al.

It is certified that error appears in the above-identified patent and that said Letters Patent is hereby corrected as shown below:

Column 6, Line 35 delete "scheme peptide," and insert therefor --c heme peptide,--.

Column 6, Line 43-44 delete "from column" and insert therefor --from a column--.

Column 6 Line 55 delete "however" and insert therefor --however,--.

Column 7, Line 39 delete "labite," and insert therefor --labile--.

Column 8, line 33 delete "an" and insert therefor --and--.

Column 8 line 45 insert --dye-- before "such as fluorescein".

Column 12, Line 60 delete "HCI" and insert therefor --HCl--.

Column 13, Line 18 delete "Cvstamine" and insert therefor --Cystamine--.

Column 13, Line 43 delete "exhibit" and insert therefor --inhibit--.

Column 14, Line 7 delete "stimulatino" and insert therefor --stimulating--.

Column 19, Line 17 delete "Phoschorylation" and insert therefor --Phosphorylation--.

Column 19, Line 42 delete "Diaminodichenvldisulfide" and insert therefor --Diaminodiphenyldisulfide--.

UNITED STATES PATENT AND TRADEMARK OFFICE
CERTIFICATE OF CORRECTION

PATENT NO. : 5,153,166
DATED : October 6, 1992
INVENTOR(S) : Jain et al.

It is certified that error appears in the above-identified patent and that said Letters Patent is hereby corrected as shown below:

Column 11, Lines 13 - 19, delete

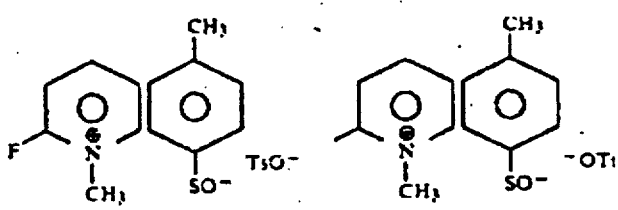

and insert therefor

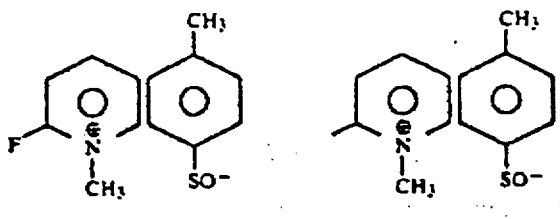

UNITED STATES PATENT AND TRADEMARK OFFICE
CERTIFICATE OF CORRECTION

PATENT NO. : 5,153,166

DATED : October 6, 1992

INVENTOR(S) : Jain et al.

It is certified that error appears in the above-identified patent and that said Letters Patent is hereby corrected as shown below:

Column 19 Line 66 delete "Trimethoxvmethvlsilane" and insert therefor --Trimethoxymethylsilane--.

Column 20 Line 23 delete "Fractocel (2) FII with Glutaraldehvde" and insert therefor --Fractogel (2) FII with Glutaraldehyde--.

Column 20 Line 32 delete "Fractocel-Boronate" and insert therefor --Fractogel-Boronate--.

Column 20 Line 33 delete "derivativ" and insert therefor --derivative--.

Column 20 Line 36 delete "(7)" and insert therefor --($\underline{7}$)--.

Column 20 Line 44 delete "Fractocel" and insert therefor --Fractogel--.

Column 21 Line 38 delete "wa" and insert therefor --was--.

Column 22, Line 53 delete "hal=a" and insert therefor --Hal=a--.

UNITED STATES PATENT AND TRADEMARK OFFICE
CERTIFICATE OF CORRECTION

PATENT NO. : 5,153,166

DATED : October 6, 1992

INVENTOR(S) : Jain et al.

It is certified that error appears in the above-identified patent and that said Letters Patent is hereby corrected as shown below:

Column 22, Line 59 delete "pluraliyto" and insert therefor --plurality--.

Signed and Sealed this

Second Day of November, 1993

Attest:

BRUCE LEHMAN

Attesting Officer

Commissioner of Patents and Trademarks